United States Patent [19]

van der Jagt

[11] Patent Number: Plant 5,871

[45] Date of Patent: Feb. 3, 1987

[54] CHRYSANTHEMUM 'PINK REFLA'

[75] Inventor: Martinus van der Jagt, Ter-Aar, Netherlands

[73] Assignee: Chrysanthemum Breeders Association N.V., Netherlands

[21] Appl. No.: 664,835

[22] Filed: Oct. 25, 1984

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Parkhurst & Oliff

[57] ABSTRACT

A new and distinct cultivar of Chrysanthemum plant named 'Pink Refla', bearing large sized pink blossoms with a green yellow center and a performance of seventeen days.

3 Drawing Figures

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of Chrysanthemum plant which is a cross of parents known as 'Flamenco' and 'Dramatic'. The new cultivar was discovered by Martinus van der Jagt in April, 1982 at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a large sized bloom and pink color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage and petiole of the new cultivar.

DESCRIPTION OF THE NEW PLANT

This new variety of chrysanthemum is of the botanical classification *Chrysanthemum morifolium,* named 'Pink Refla'. When grown in the vicinity of Ter Aar, Holland, it has a response time of approximately eight and one-half weeks. This new variety produces large sized pink blooms with a green yellow center having a performance of seventeen days. This new variety of Chrysanthemum has been found to retain its distinctive characteristics throughout successive propagations and may be planted under conventional greenhouse conditions in Holland between weeks 01–34.

The following is a description of the plant and characteristics that distinguish it over related known varieties and its antecedents:

Botanical classification: *Chrysanthemum morifolium.*

Bud:

*Size.*—Medium.

*Form.*—Flat top.

*Color.*—Spinel pink RHS 0625/2.

Bloom:

*Size.*—Large.

*Fully expanded.*—7–9 cm.

*Borne.*—Single.

*Stems.*—Strong.

*Forms.*—Semi-double.

*Permanence.*—17 days.

Color:

*Center of flower (Disk Floret).*—Parsley Green RHS 00962/1+Cadmium Orange RHS 8/2.

*Base of petals.*—Spinel Pink RHS 0625/3.

*Inside of petals.*—Phlox Pink RHS 625/3.

*Reverse of petals.*—Neyron Rose RHS 623/3.

*Outer petals.*—Phlox Pink RHS 625/3.

*Tonality from a distance.*—Attractive flower, with fading pink color over its petals.

*Discoloration.*—Beginning to maturity — Spinel Pink RHS 0625/3 to Phlox Pink RHS 625/3. Maturity—Phlox Pink RHS 625/3 to Neyron Rose RHS 623/3.

Petals:

*Texture (upper and underside).*—Rough.

*Number.*—26–40.

*Cross-section.*—Generally flat including keels.

*Arrangement.*—Imbricated.

*Size.*—Length 3–3.5 cm. and width 1–1.5 cm. (approx.).

*Persistence.*—Petals rather strong. A little bit reflexion at edge when over-bloomed.

*Fragrance.*—Chrysanthemum.

Reproductive organs:

*Stamen.*—Normal.

*Pollen.*—A few appear when blooming.

*Styles.*—Columnar; Green-yellow.

*Length.*—6–7 mm. (approx.).

*Stigmas.*—Normal Yellow; width 1.5 mm. (approx.).

*Ovaries.*—Enclosed in calyx.

Plant:

*Form.*—Herbaceous.

*Growth.*—Vigorous.

*Height.*—Tall, approx. 110 cms.

*Peduncle.*—Strong.

*Response time.*—8.5 to 9 weeks.

Foliage:

*Color.*—Normal green.

*Size.*—Length 12.5 cm. and width 8 cm. (approx.).

*Quantity.*—Normal to less.

*Shape.*—Pointed.

*Texture.*—Upperside — Rough. Underside — Smooth.

*Ribs and veins.*—Normal.

*Margin.*—Deep undulated.

*Leaf underside.*—Smooth to heavy.

In the description above, color references are made to The "Horticultural Colour Chart I & II" issued by the British Colour Council in collaboration with The Royal Horticultural Society, Copyright Robert F. Wilson, Vol I, 1938; Vol II, 1941, printed by Henry Stone & Son, Ltd., Banbury, England.

What is claimed is:

1. A new and distinct cultivar of Chrysanthemum named 'Pink Refla', as described and illustrated in the foregoing specification and accompanying drawings.

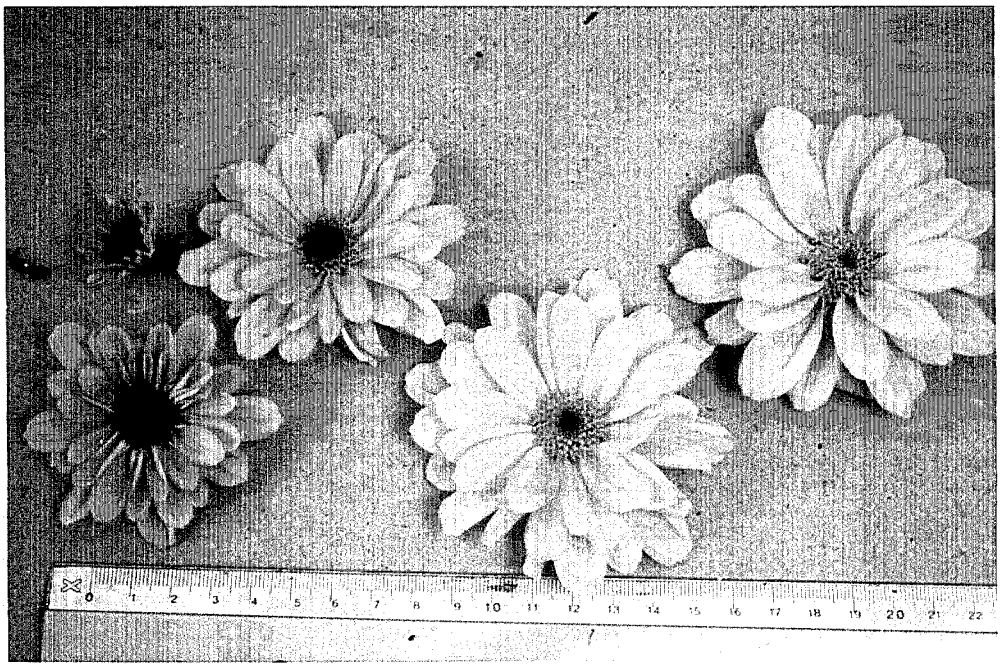

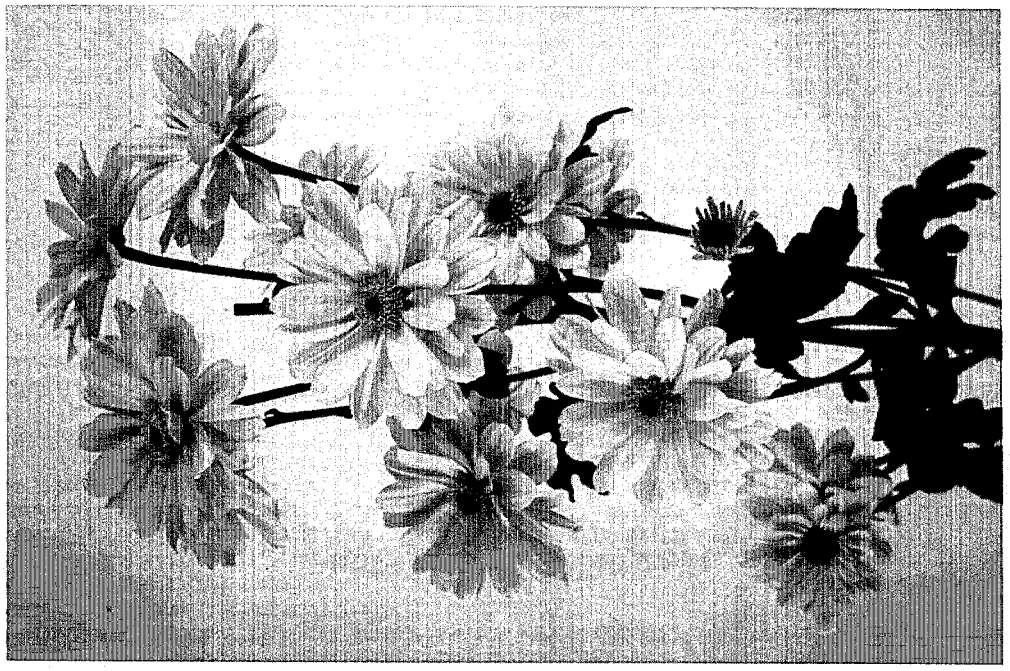
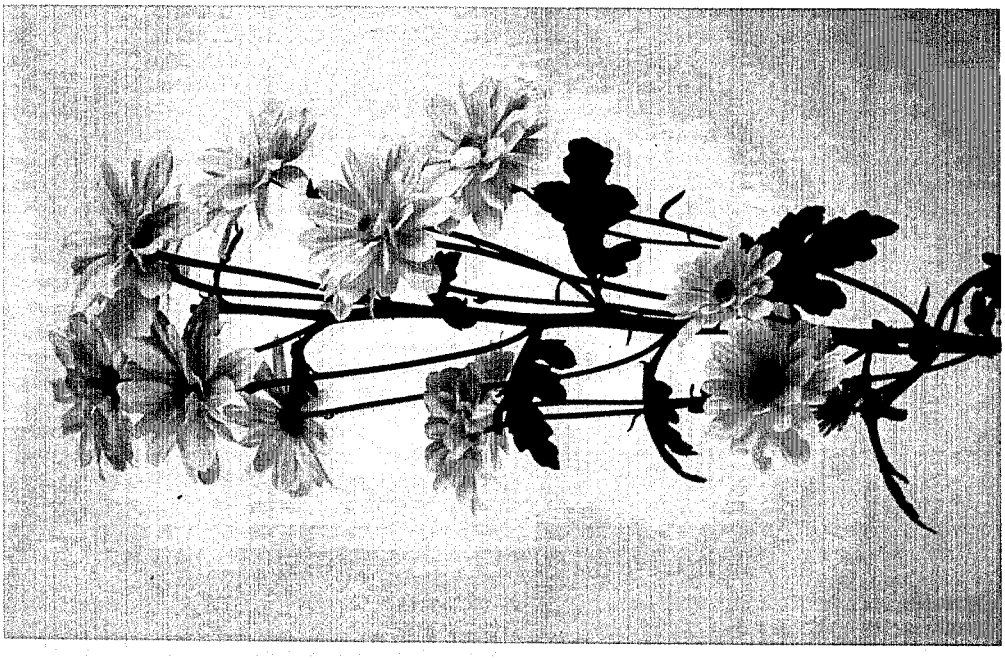

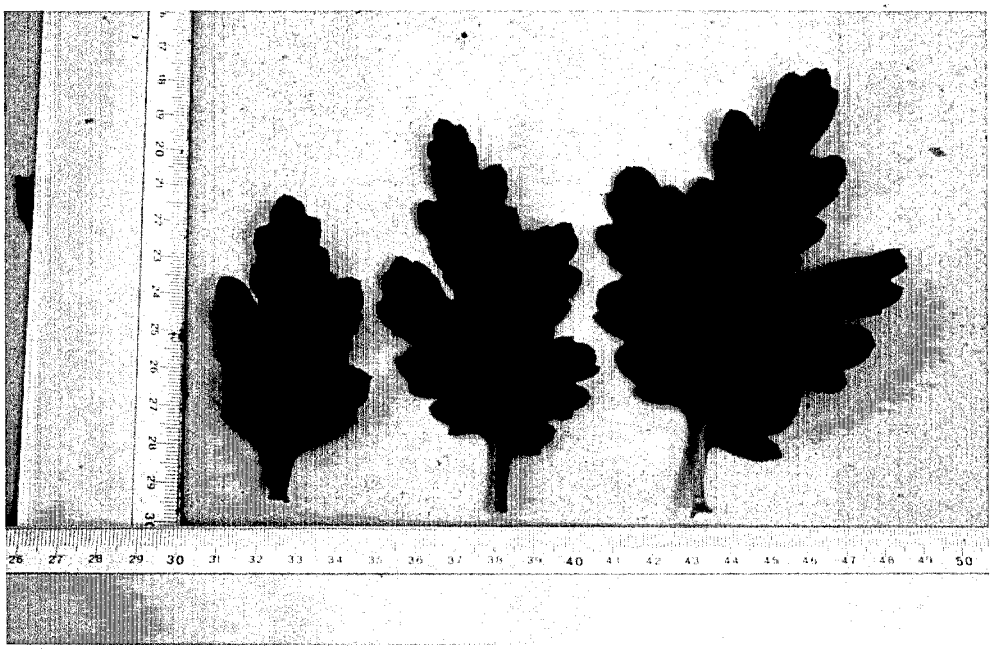
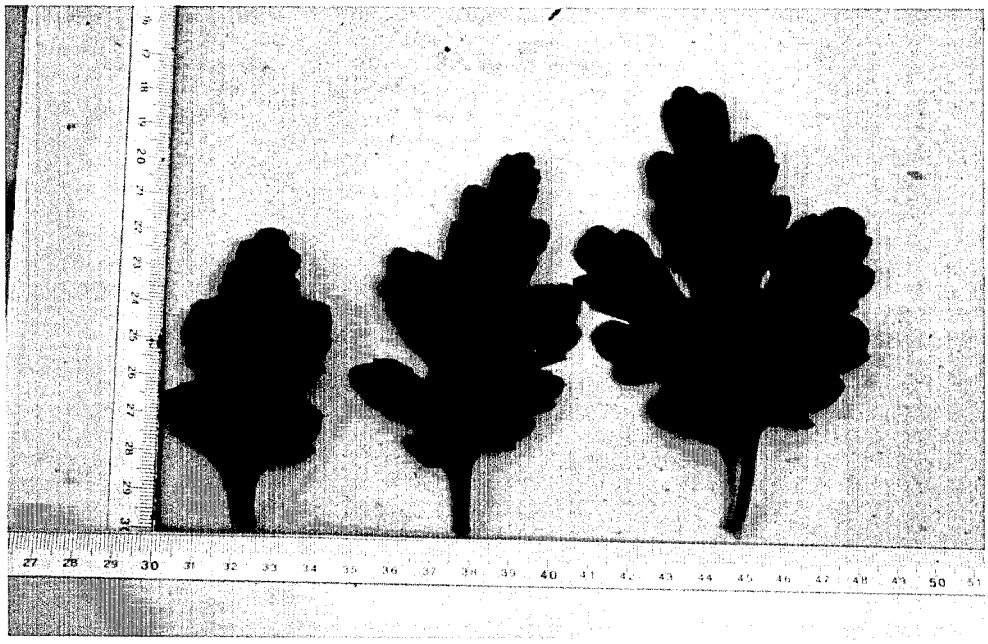

* * * * *